United States Patent
Guillard et al.

(10) Patent No.: US 10,730,749 B2
(45) Date of Patent: Aug. 4, 2020

(54) PROCESS FOR INTEGRATING A PARTIAL OXIDATION PLANT WITH AN OXY-COMBUSTION PLANT UTILIZING A STEAM TURBINE

(71) Applicant: L'Air Liquide, Société Anonyme pour l'Etude et l'Exploitation des Procédés Georges Claude, Paris (FR)

(72) Inventors: Alain Guillard, Houston, TX (US); Alexander Roesch, Frankfurt (DE)

(73) Assignee: L'Air Liquide, Société Anonyme pour l'Etude et l'Exploitation des Procédés Georges Claude, Paris (FR)

( * ) Notice: Subject to any disclaimer, the term of this patent is extended or adjusted under 35 U.S.C. 154(b) by 78 days.

(21) Appl. No.: 16/183,345

(22) Filed: Nov. 7, 2018

(65) Prior Publication Data

US 2020/0140270 A1 May 7, 2020

(51) Int. Cl.
| | |
|---|---|
| *C01B 3/36* | (2006.01) |
| *C01C 1/04* | (2006.01) |
| *C01B 32/50* | (2017.01) |
| *C07C 29/151* | (2006.01) |
| *C01B 3/02* | (2006.01) |

(52) U.S. Cl.
CPC ............... *C01B 3/36* (2013.01); *C01B 3/025* (2013.01); *C01B 32/50* (2017.08); *C01C 1/04* (2013.01); *C07C 29/1512* (2013.01); *C01B 2203/0255* (2013.01); *C01B 2203/061* (2013.01); *C01B 2203/068* (2013.01); *C01B 2203/0805* (2013.01); *C01B 2203/84* (2013.01)

(58) Field of Classification Search
CPC combination set(s) only.
See application file for complete search history.

(56) References Cited

U.S. PATENT DOCUMENTS

| | | | | |
|---|---|---|---|---|
| 3,738,940 | A * | 6/1973 | Buschmann et al. ... | C01B 3/363 252/373 |
| 3,874,592 | A * | 4/1975 | Buschmann ............ | C01B 3/363 239/132.3 |
| 4,887,962 | A * | 12/1989 | Hasenack ............... | F23D 14/78 110/263 |
| 6,293,084 | B1 * | 9/2001 | Drnevich ............... | B01D 53/22 60/39.17 |
| 7,465,324 | B2 * | 12/2008 | Filippi .................. | B01J 8/0285 423/418.2 |
| 9,969,666 | B1 * | 5/2018 | Roesch .................. | C07C 31/04 |
| 2010/0299997 | A1 * | 12/2010 | Hoteit ...................... | C01B 3/46 48/210 |

(Continued)

*Primary Examiner* — Kaity V Chandler
(74) *Attorney, Agent, or Firm* — Elwood L. Haynes

(57) ABSTRACT

A method of co-producing a carbon dioxide containing stream and a syngas stream, including introducing a high-pressure hydrocarbon containing stream and a high-pressure oxygen containing stream into a syngas generator, thereby producing a high-pressure syngas stream, introducing a low-pressure hydrocarbon containing stream and a low-pressure oxygen containing stream into an oxy-combustion device, thereby producing a low-pressure carbon dioxide containing stream, and introducing the low-pressure carbon dioxide containing stream into a waste heat boiler, thereby producing steam, and introducing the steam into a work expander, thereby generating work and a carbon dioxide containing stream.

20 Claims, 6 Drawing Sheets

(56) References Cited

U.S. PATENT DOCUMENTS

| | | | |
|---|---|---|---|
| 2012/0272657 A1* | 11/2012 | Baker | B01D 53/22 |
| | | | 60/772 |
| 2015/0226118 A1* | 8/2015 | Kelly | F02C 3/22 |
| | | | 290/52 |
| 2015/0226428 A1* | 8/2015 | Dubettier-Grenier | F23L 7/007 |
| | | | 110/348 |
| 2015/0267611 A1* | 9/2015 | Nemitallah | F02C 3/20 |
| | | | 60/776 |
| 2016/0083811 A1* | 3/2016 | Motamedhashemi | C01B 3/508 |
| | | | 75/493 |
| 2017/0158504 A1* | 6/2017 | Merritt, Jr. | C01B 3/56 |
| 2017/0241338 A1* | 8/2017 | Forrest | F02C 3/22 |
| 2018/0128172 A1* | 5/2018 | Allam | C10K 3/04 |
| 2018/0370796 A1* | 12/2018 | Mokheimer | C01B 3/382 |

\* cited by examiner

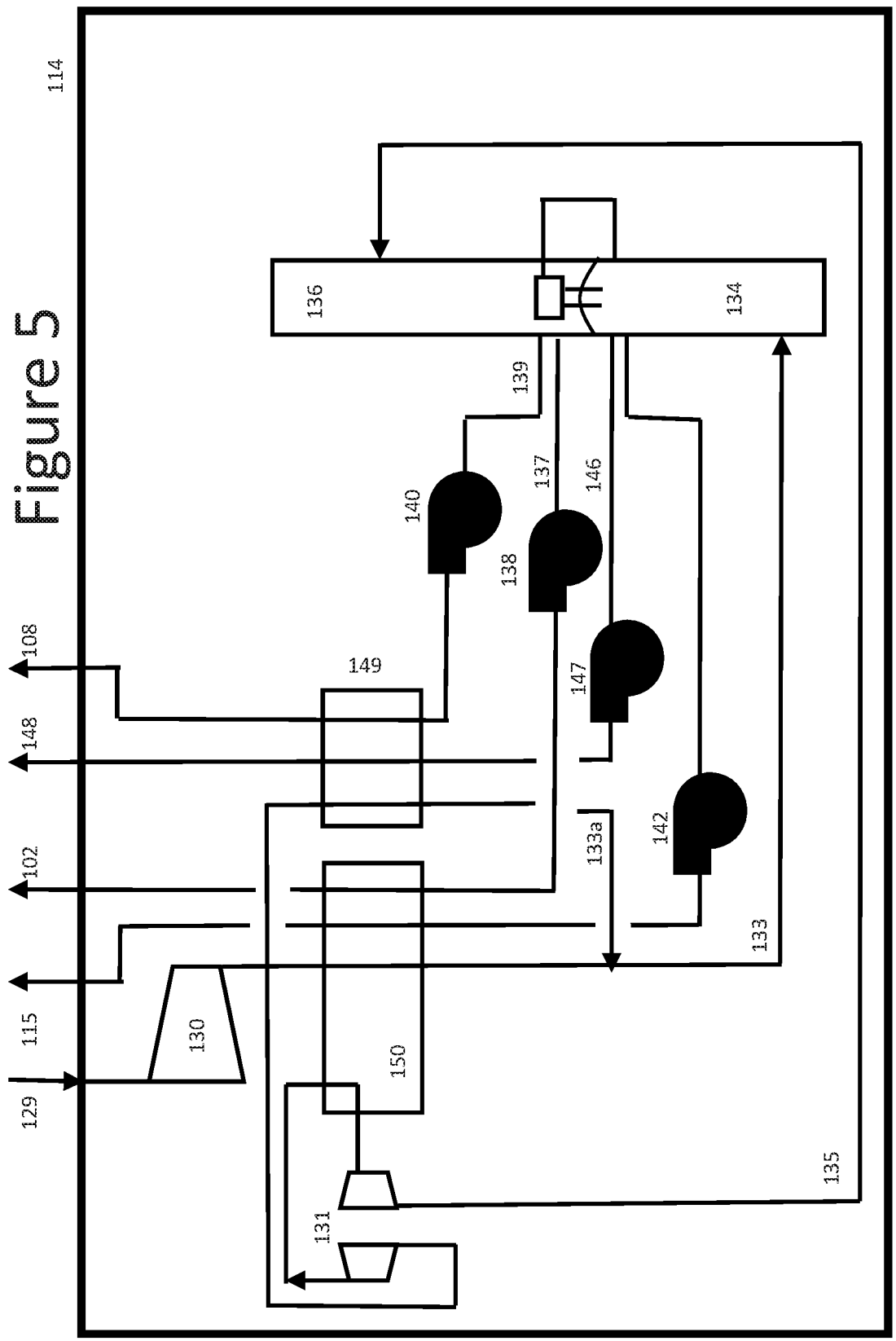

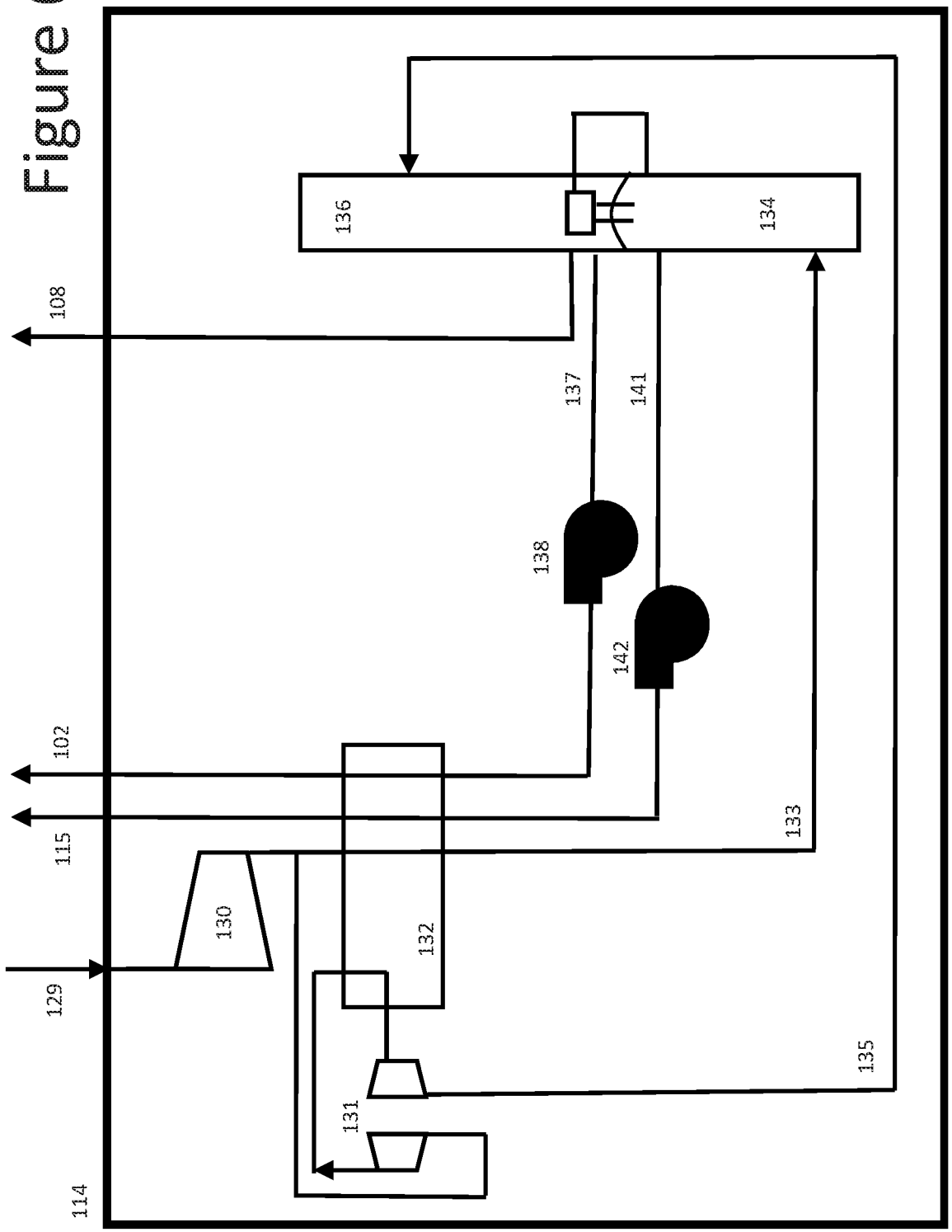

PROCESS FOR INTEGRATING A PARTIAL OXIDATION PLANT WITH AN OXY-COMBUSTION PLANT UTILIZING A STEAM TURBINE

BACKGROUND

Today's challenge is to offer technical solutions with significant emission reductions without jeopardizing project economics. Priorities include technical risk as well as a safe and reliable operation.

There is an industry need to address the integration of tailored air separation unit, an oxycombustion power generation process and a high-pressure partial oxidation based synthesis gas generation plant.

Comparing this novel process integration with the state of the art stand-alone process units, the overall operating and capital expenditures will be reduced and the direct and indirect CO2 and criteria pollutants such as SOX, NOX, CO, VOC, particles will be significantly reduced.

SUMMARY

A method of co-producing a carbon dioxide containing stream and a syngas stream, including introducing a high-pressure hydrocarbon containing stream and a high-pressure oxygen containing stream into a syngas generator, thereby producing a high-pressure syngas stream, introducing a low-pressure hydrocarbon containing stream and a low-pressure oxygen containing stream into an oxy-combustion device, thereby producing a low-pressure carbon dioxide containing stream, and introducing the low-pressure carbon dioxide containing stream into a waste heat boiler, thereby producing steam, and introducing the steam into a work expander, thereby generating work and a carbon dioxide containing stream.

BRIEF DESCRIPTION OF THE DRAWINGS

For a further understanding of the nature and objects for the present invention, reference should be made to the following detailed description, taken in conjunction with the accompanying drawings, in which like elements are given the same or analogous reference numbers and wherein:

FIG. 5 is a schematic representation of further details of the air separation unit, in accordance with one embodiment of the present invention.

FIG. 6 is a schematic representation of further details of the air separation unit, in accordance with one embodiment of the present invention.

DESCRIPTION OF PREFERRED EMBODIMENTS

Figure 1:
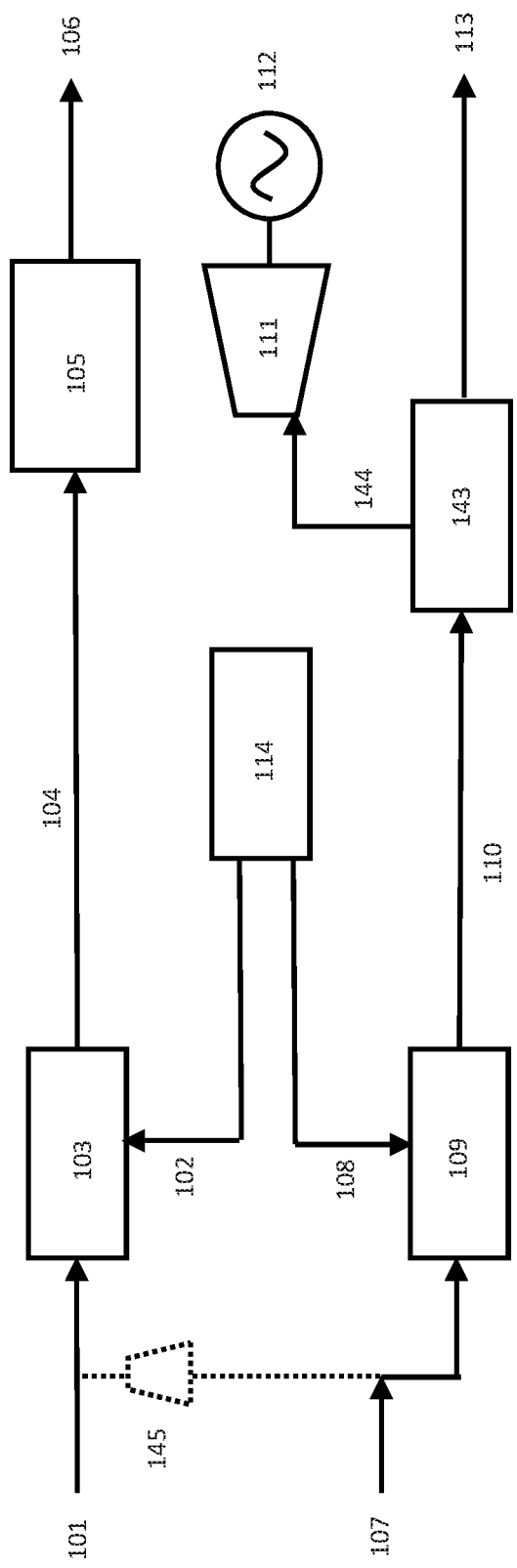
FIG. 1 is a schematic representation of a process for integration of an air separation unit, a partial oxidation syngas unit, and an oxy-combustion unit in accordance with one embodiment of the present invention.
Figure 2:
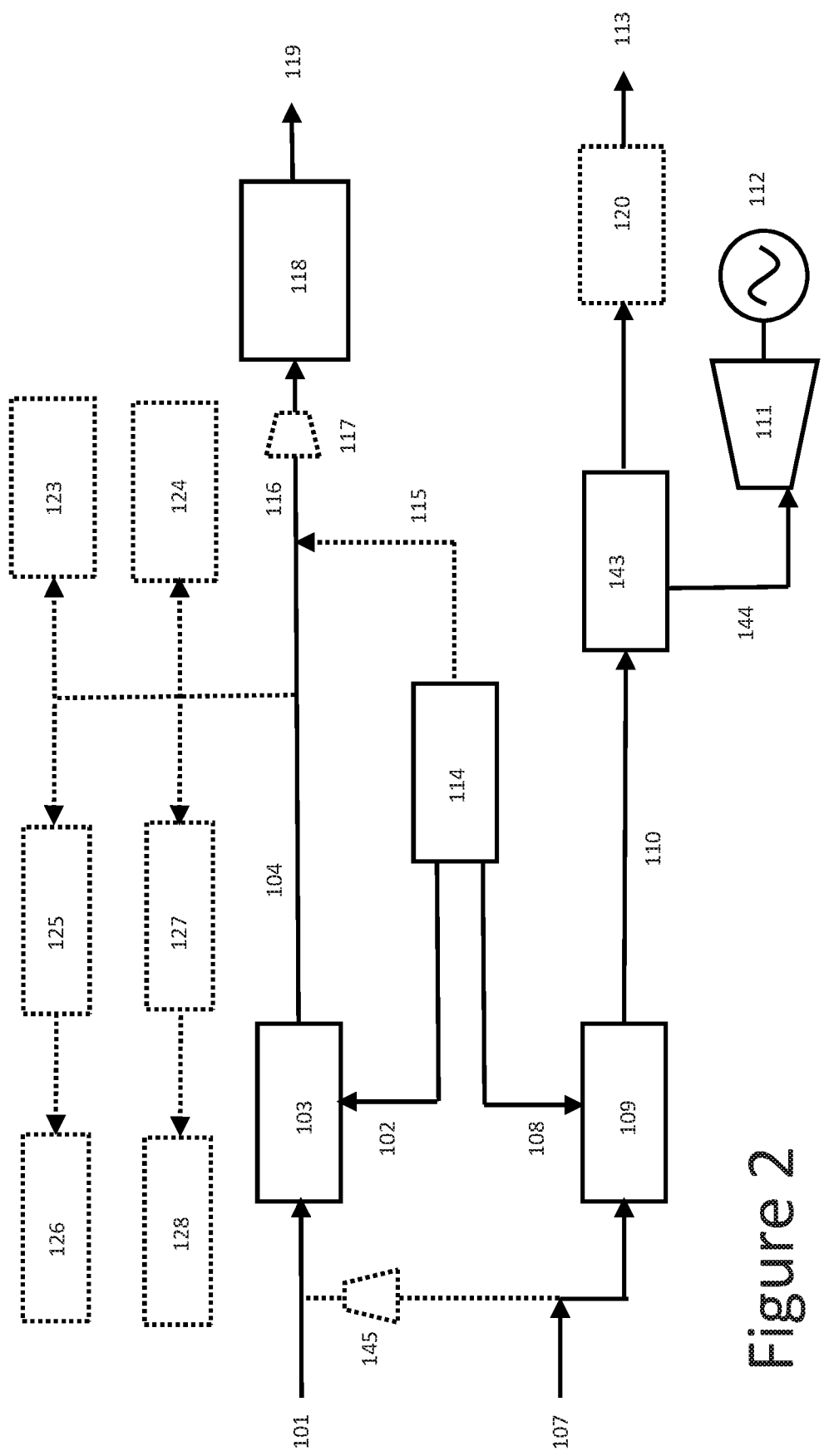
FIG. 2 is a schematic representation of a process for integration of an air separation unit, a partial oxidation syngas unit, an oxy-combustion unit, and an ammonia reactor with details of possible downstream devices, in accordance with one embodiment of the present invention.
Figure 3:
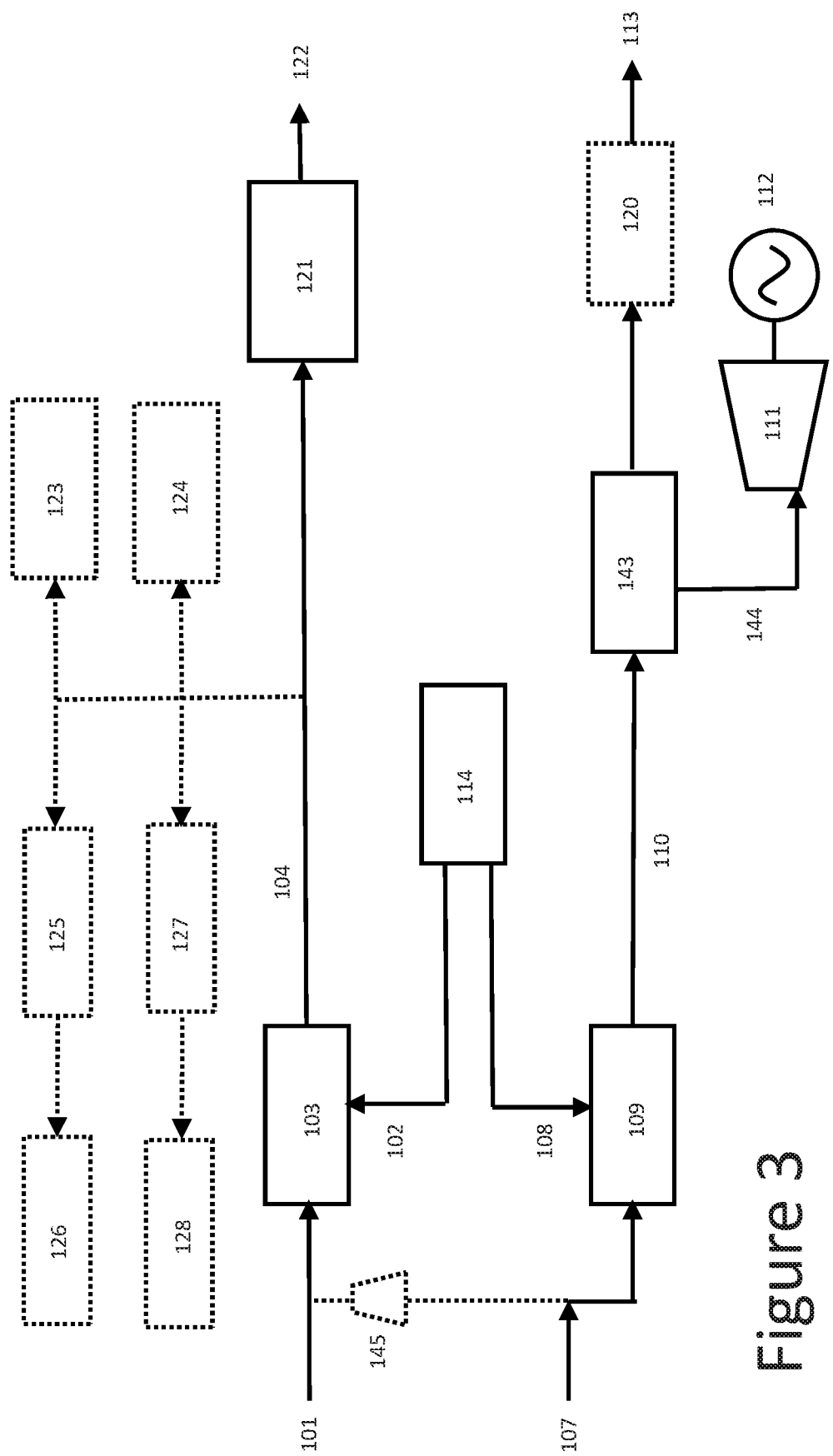
FIG. 3 is a schematic representation of a process for integration of an air separation unit, a partial oxidation syngas unit, an oxy-combustion unit, and a methanol reactor with details of possible downstream devices, in accordance with one embodiment of the present invention.

Element Numbers:
101=high-pressure hydrocarbon containing stream
102=high-pressure oxygen containing stream
103=syngas generator
104=high-pressure syngas stream
105=product reactor
106=product stream
107=low-pressure hydrocarbon containing stream
108=low-pressure oxygen containing stream
109=oxy-combustion device
110=low-pressure carbon dioxide containing stream
111=work expander
112=work (generated by work expander)
113=carbon dioxide containing stream
114=air separation unit
115=high-pressure nitrogen containing stream
116=ammonia reactor feed stream
117=ammonia reactor feed stream compressor
118=ammonia reactor
119=ammonia product stream
120=carbon dioxide separator
121=methanol reactor
122=methanol product stream
123=downstream metallurgical process
124=downstream oxy-alcohol reactor
125=second carbon dioxide separator
126=second carbon dioxide product stream
127=hydrogen separator
128=hydrogen product stream
129=feed air stream (to air separation unit)
130=main air compressor
131=booster/expander
132=main heat exchanger
133=cooled feed air to HP column
134=HP column
135=cooled/expanded air to LP column
136=LP column
137=first liquid oxygen stream
138=first liquid oxygen stream pump
139=second liquid oxygen stream
140=second liquid oxygen stream pump
141=first liquid nitrogen stream
142=first liquid nitrogen stream pump
143=waste heat boiler
144=steam stream (to work expander)
145=optional hydrocarbon containing stream compressor
146=second liquid nitrogen stream
147=second liquid nitrogen stream pump
148=low-pressure nitrogen containing stream
149=first split core heat exchanger
150=second split core heat exchanger Illustrative examples of the invention are described below. While the invention is susceptible to various modifications and alternative forms, specific embodiments thereof have bene shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

It will of course be appreciated that in the development of any such actual embodiment, numerous implementation -specific decisions must be made to achieve the developer's goals, such as compliance with system-related and business-related constraints, which will vary from one implementation to another. Moreover, it will be appreciated that such development effort might be complex and time-consuming, but would nevertheless be a routine undertaking for those of ordinary skill in the art having the benefit of this disclosure.

Turning now to FIGS. 1-6, a method of coproducing a carbon dioxide containing stream and a syngas stream is provided. A high-pressure hydrocarbon containing stream 101 and a high-pressure oxygen containing stream 102 are introduced into a syngas generator 103, thereby producing a high-pressure syngas stream 104. Syngas generator 103 may be a partial oxidation reactor or an autothermal reactor.

At least a portion of the high-pressure syngas 104 may be introduced into a second carbon dioxide separator 125 and thus be used to produce a second carbon dioxide product stream 126. At least a portion of the high-pressure syngas 104 may be introduced into a hydrogen separator 127 and thus be used to produce a hydrogen product stream 128.

As used herein, the term "high-pressure" is defined as meaning having a pressure of greater than 10 barg, preferably greater than 50 barg. One embodiment of the present invention, high-pressure syngas stream 104 may be used in downstream processes involving the synthesis of ammonia or methanol. As these processes typically operate at pressures above 100 barg, the term "high-pressure" as used herein preferably means having a pressure equal to or greater than 100 barg. High-pressure hydrocarbon containing stream 101 may be at the pressure required by syngas generator 103 to produce high-pressure syngas stream 104.

A low-pressure hydrocarbon containing stream 107 and a low-pressure oxygen containing stream 108 are introduced into an oxy-combustion device 109, thereby producing a low-pressure carbon dioxide containing stream 110. Carbon dioxide containing stream 113 may be suitable for downstream separation 120.

Low-pressure carbon dioxide containing stream 110 is then introduced into a waste boiler 143, therein producing a steam stream 144. Steam stream 144 is then introduced into work expander 111, thereby generating work 112. Low-pressure carbon dioxide containing stream 113 may be separated in a downstream carbon dioxide separator 120. The resulting carbon dioxide product stream 113 may be exported.

High-pressure syngas stream 104 may be suitable for producing a downstream product 106. In one embodiment the downstream product may be a metallurgical process 123 or may be an oxy-alcohol process 124. High-pressure syngas stream 104 may be suitable for producing a downstream product 106 without further syngas compression. Downstream product may be methanol 122 produced in a methanol reactor 121.

Downstream product may be ammonia 119 produced in an ammonia reactor 118. A high-pressure nitrogen stream 115 may be combined with high-pressure syngas stream 104, thereby producing an ammonia reactor feed stream 116, which is then introduced into the ammonia reactor 118. High-pressure nitrogen stream 115 may not be subject to further nitrogen compression. In one embodiment of the present invention ammonia reactor feed stream 116 is further compressed in feed compressor 117. High-pressure oxygen stream 102 and high-pressure nitrogen containing stream 115 may be produced in the same air separation unit 114. High-pressure oxygen stream 102, high-pressure nitrogen containing stream 115, and low-pressure oxygen stream 108 may be produced in the same air separation unit 114.

Figure 4:
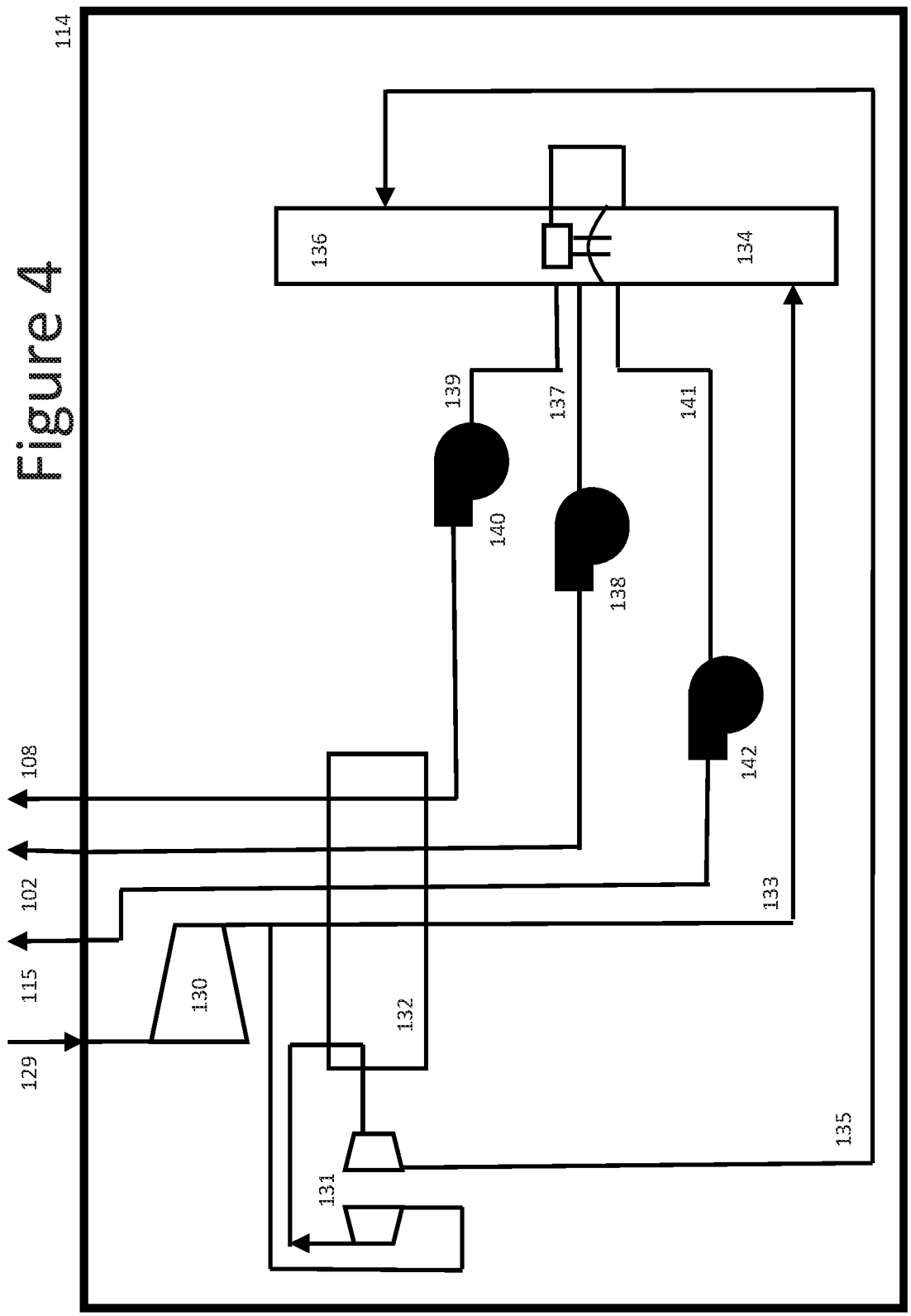
FIG. 4 is a schematic representation of further details of the air separation unit, in accordance with one embodiment of the present invention.

As illustrated in FIG. 4, air separation unit 114 may operate in a pumping cycle. In a pumping cycle, cryogenic pumps 138/140/142 are used to pressurize liquid oxygen 137/139 or liquid nitrogen 141, which is then vaporized to produce pressurized gaseous product streams 102/108/115. In this process, feed air stream 129 is cooled in main heat exchanger 132 against the liquid cryogen streams, which are thus vaporized. As a means of controlling the throughput, feed air stream 129 is compressed 130, then split into two separate streams 133/135. The first stream 133 is directed through main heat exchanger 132 and is then introduced into the HP column 134 of air separation unit 114.

Second stream 135 is further compressed 131 to an intermediate pressure, and hence adding additional energy required to produce vaporized oxygen. The cooled second stream 135 is then expanded 131 to produce cold and this cold, expanded stream is then introduced into the LP column 136 of air separation unit 114. Thus, in one embodiment, high-pressure oxygen stream 102 and high-pressure nitrogen stream 115 are produced by vaporizing a first high-pressure liquid oxygen stream 137 and a high-pressure liquid nitrogen stream 141 in a main heat exchanger 132. In another embodiment, high-pressure oxygen stream 102, high-pressure nitrogen stream 115, and low-pressure oxygen stream 108 are produced by vaporizing a first liquid oxygen stream 137, a liquid nitrogen stream 141, and a second liquid oxygen stream 139 in a main heat exchanger 132. In one embodiment, high-pressure nitrogen stream 115 is not subject to further nitrogen compression.

In the cycle represented in FIG. 4, all of the pressurized cryogenic streams are vaporized in a single heat exchanger. However, as illustrated in FIG. 5, in another embodiment of the present invention, a split core heat exchanger design may be employed. The system presented in FIG. 5 is identical to that presented in FIG. 4, and the common streams will not be redefined here. Likewise, in the interest of simplifying FIG. 5, the Booster/Expander 131 is only shown being reintroduced in one of the split core heat exchangers (in this case, second split core heat exchanger 150), however this cooling stream may be introduced in either or both of the split core heat exchangers.

However, this system introduces a second liquid nitrogen stream 146, which is pressurized in second liquid nitrogen stream pump 147. This second pressurized liquid nitrogen stream is then vaporized, along with the other low-pressure stream, low-pressure oxygen containing stream 108, against compressed feed air stream 133 in a first split core heat exchanger 148. Also, the gaseous high-pressure streams, high-pressure oxygen containing stream 102 and high-pressure nitrogen containing stream 115, are vaporized against a portion of compressed feed air stream 133a in a second split core heat exchanger 150.

As illustrated in FIG. 6, in another embodiment of the present invention, low-pressure oxygen containing stream 108 may be removed in vapor phase and not pass through main heat exchanger 132.

It will be understood that many additional changes in the details, materials, steps and arrangement of parts, which have been herein described in order to explain the nature of the invention, may be made by those skilled in the art within the principle and scope of the invention as expressed in the appended claims. Thus, the present invention is not intended to be limited to the specific embodiments in the examples given above.

What is claimed is:

1. A method of co-producing a carbon dioxide containing stream and a syngas stream, comprising:

introducing a high-pressure hydrocarbon containing stream and a high-pressure oxygen containing stream into a syngas generator, thereby producing a high-pressure syngas stream, introducing a low-pressure hydrocarbon containing stream and a low-pressure oxygen containing stream into an oxy-combustion device, thereby producing a low-pressure carbon dioxide containing stream, and introducing the low-pressure carbon dioxide containing stream into a waste heat boiler, thereby producing steam, and introducing the steam into a work expander, thereby generating work and a carbon dioxide containing stream.

2. The method of claim 1, wherein the high-pressure syngas stream is suitable for producing a downstream product.

3. The method of claim 1, wherein the high-pressure syngas stream is suitable for producing a downstream product without further syngas compression.

4. The method of claim 1, wherein the carbon dioxide containing stream is suitable for downstream separation.

5. The method of claim 1, wherein the downstream product is methanol produced in a methanol reactor.

6. The method of claim 1, wherein the downstream product is ammonia produced in an ammonia reactor.

7. The method of claim 6, wherein a high-pressure nitrogen stream is combined with the high-pressure syngas stream, thereby producing an ammonia reactor feed stream, which is then introduced into the ammonia reactor.

8. The method of claim 7, wherein the ammonia reactor feed stream is further compressed in a feed compressor.

9. The method of claim 7, wherein the high-pressure oxygen stream, the low-pressure oxygen stream, and the high-pressure nitrogen containing stream are produced in the same air separation unit.

10. The method of claim 9, wherein the high-pressure oxygen stream, the high-pressure nitrogen stream, and the low-pressure oxygen stream are produced by vaporizing a high-pressure liquid oxygen stream, a high-pressure liquid nitrogen stream, and a low-pressure liquid oxygen stream in a main heat exchanger.

11. The method of claim 9, wherein:

the high-pressure oxygen stream and the high-pressure nitrogen stream are produced by vaporizing a high-pressure liquid oxygen stream and a high-pressure liquid nitrogen stream in a first heat exchanger, and the low-pressure oxygen stream and a low-pressure nitrogen stream are produced by vaporizing a low-pressure liquid oxygen stream and a low-pressure liquid nitrogen stream in a second heat exchanger.

12. The method of claim 9, wherein:

the high-pressure oxygen stream and the high-pressure nitrogen stream are produced by vaporizing a high-pressure liquid oxygen stream and a high-pressure liquid nitrogen stream in the main heat exchanger, and the low-pressure oxygen stream is not vaporized in a heat exchanger.

13. The method of claim 10, wherein the high-pressure nitrogen stream is not subject to further nitrogen compression.

14. The method of claim 1, wherein the syngas generator comprises a partial oxidation reactor.

15. The method of claim 1, wherein the syngas generator comprises an autothermal reactor.

16. The method of claim 1, wherein the high-pressure syngas stream has a pressure equal to or greater than about 50 barg.

17. The method of claim 1, wherein the high-pressure syngas stream has a pressure equal to or greater than about 80 barg.

18. The method of claim 1, wherein the high-pressure syngas stream has a pressure equal to or greater than about 100 barg.

19. The method of claim 1, wherein the high-pressure hydrocarbon containing stream is at the same pressure as required by the syngas generator.

20. The method of claim 1, wherein at least a portion of the high-pressure syngas stream is used as feedstock for an oxy-alcohol reactor.

* * * * *